US009269544B2

(12) United States Patent
Koo et al.

(10) Patent No.: US 9,269,544 B2
(45) Date of Patent: Feb. 23, 2016

(54) SYSTEM AND METHOD FOR TREATMENT OF BIOFILMS

(71) Applicant: Colorado State University Research Foundation, Fort Collins, CO (US)

(72) Inventors: Il-Gyo Koo, Daegu (KR); Myeong Yeol Choi, Fort Collins, CO (US); Doreene Hyatt, Fort Collins, CO (US); Amber Zagrodzki, Palmer Lake, CO (US); Dean A. Hendrickson, Fort Collins, CO (US); George J. Collins, Fort Collins, CO (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 40 days.

(21) Appl. No.: 14/155,636

(22) Filed: Jan. 15, 2014

(65) Prior Publication Data

US 2014/0225495 A1     Aug. 14, 2014

Related U.S. Application Data

(60) Provisional application No. 61/763,265, filed on Feb. 11, 2013.

(51) Int. Cl.
*H05H 1/28*        (2006.01)
*H01J 37/32*     (2006.01)
*H05H 1/24*        (2006.01)
(Continued)

(52) U.S. Cl.
CPC ......... *H01J 37/32431* (2013.01); *A61B 18/042* (2013.01); *H05H 1/2406* (2013.01); *H05H 1/28* (2013.01); *A61B 2018/00023* (2013.01); *H05H 2001/2431* (2013.01)

(58) Field of Classification Search
CPC ........................ H05H 2001/2431; H05H 1/28
USPC ...................................................... 313/13, 22
See application file for complete search history.

(56) References Cited

U.S. PATENT DOCUMENTS

| 3,434,476 A | 3/1969 | Shaw et al. |
| 3,492,074 A | 1/1970 | Rendina |
| 3,687,832 A | 8/1972 | Fydelor et al. |

(Continued)

FOREIGN PATENT DOCUMENTS

| CN | 2391565 Y | 8/2000 |
| DE | 3710489 A1 | 11/1987 |

(Continued)

OTHER PUBLICATIONS

U.S. Appl. No. 08/383,162, filed Feb. 3, 1995, Lawrence K. Pacer.
(Continued)

*Primary Examiner* — Nimeshkumar Patel
*Assistant Examiner* — Christopher Raabe

(57) ABSTRACT

A plasma system is disclosed. The system includes a plasma device including an inner electrode and an outer electrode coaxially disposed around the inner electrode, wherein at least one of the inner electrode and the outer electrode is temperature controlled; an ionizable media source coupled to the plasma device and configured to supply ionizable media thereto; and a power source coupled to the inner and outer electrodes and configured to ignite the ionizable media at the plasma device to form a plasma effluent.

15 Claims, 6 Drawing Sheets

(51) Int. Cl.
*A61B 18/04* (2006.01)
*A61B 18/00* (2006.01)

(56) References Cited

U.S. PATENT DOCUMENTS

| | | | |
|---|---|---|---|
| 3,903,891 A | 9/1975 | Brayshaw | |
| 3,991,764 A | 11/1976 | Incropera et al. | |
| 4,140,892 A * | 2/1979 | Muller | 219/121.47 |
| 4,188,426 A | 2/1980 | Auerbach | |
| 4,242,562 A | 12/1980 | Karinsky et al. | |
| 4,313,783 A | 2/1982 | Davies et al. | |
| 4,517,495 A | 5/1985 | Piepmeier | |
| 4,699,082 A | 10/1987 | Hakim | |
| 4,822,557 A | 4/1989 | Suzuki et al. | |
| 4,837,484 A | 6/1989 | Eliasson et al. | |
| 5,013,959 A | 5/1991 | Kogelschatz | |
| 5,041,110 A | 8/1991 | Fleenor | |
| 5,194,740 A | 3/1993 | Kogelschatz et al. | |
| 5,466,424 A | 11/1995 | Kusano et al. | |
| 5,776,255 A | 7/1998 | Asaba et al. | |
| 5,780,862 A | 7/1998 | Siess | |
| 5,785,807 A | 7/1998 | Kanai et al. | |
| 5,866,871 A | 2/1999 | Birx | |
| 5,869,832 A | 2/1999 | Wang et al. | |
| 5,892,328 A | 4/1999 | Shang et al. | |
| 5,945,790 A | 8/1999 | Schaefer | |
| 6,153,852 A | 11/2000 | Blutke et al. | |
| 6,172,324 B1 | 1/2001 | Birx | |
| 6,365,063 B2 | 4/2002 | Collins et al. | |
| 6,376,972 B1 | 4/2002 | Tarasenko et al. | |
| 6,407,513 B1 | 6/2002 | Vollkommer et al. | |
| 6,488,825 B1 | 12/2002 | Hilliard | |
| 6,501,079 B1 | 12/2002 | Furuya | |
| 6,758,948 B2 | 7/2004 | Johnson | |
| 7,361,175 B2 | 4/2008 | Suslov | |
| 7,429,714 B2 | 9/2008 | DePetrillo et al. | |
| 2003/0038912 A1 | 2/2003 | Broer et al. | |
| 2003/0042131 A1 | 3/2003 | Johnson | |
| 2004/0173573 A1 | 9/2004 | Igarashi et al. | |
| 2005/0149012 A1 | 7/2005 | Penny et al. | |
| 2005/0153159 A1 | 7/2005 | Sugiyama et al. | |
| 2005/0230047 A1 | 10/2005 | Collins et al. | |
| 2006/0004354 A1 | 1/2006 | Suslov | |
| 2006/0027324 A1 | 2/2006 | Makino et al. | |
| 2006/0081558 A1 | 4/2006 | Collins et al. | |
| 2006/0088655 A1 | 4/2006 | Collins et al. | |
| 2006/0091109 A1 | 5/2006 | Partlo et al. | |
| 2006/0283549 A1 | 12/2006 | Aramaki et al. | |
| 2007/0027440 A1 | 2/2007 | Altshuler et al. | |
| 2007/0029500 A1 | 2/2007 | Coulombe et al. | |
| 2007/0045561 A1 | 3/2007 | Cooper | |
| 2008/0122368 A1 | 5/2008 | Saito et al. | |
| 2009/0001052 A1 | 1/2009 | Makino et al. | |
| 2010/0125267 A1 | 5/2010 | Lee et al. | |
| 2010/0268205 A1 * | 10/2010 | Manwaring et al. | 606/29 |
| 2012/0029506 A1 | 2/2012 | Johnson | |

FOREIGN PATENT DOCUMENTS

| | | |
|---|---|---|
| DE | 4139029 A1 | 6/1993 |
| DE | 4326037 A1 | 2/1995 |
| DE | 9117019 U1 | 3/1995 |
| DE | 19524645 A1 | 2/1997 |
| DE | 19537897 A1 | 3/1997 |
| DE | 9117299 U1 | 3/2000 |
| DE | 19848784 A1 | 5/2000 |
| DE | 29724247 U1 | 8/2000 |
| EP | 0956827 A1 | 11/1999 |
| EP | 2147651 A1 | 1/2010 |
| FR | 1340509 A | 10/1963 |
| JP | 61-159953 A | 7/1986 |
| JP | H11251304 A | 9/1999 |
| JP | 2000-286094 A | 10/2000 |
| JP | 2010-242857 A | 10/2010 |
| SU | 1438745 A1 | 11/1988 |
| WO | 2004030551 A1 | 4/2004 |
| WO | 2009/080273 A1 | 7/2009 |

OTHER PUBLICATIONS

U.S. Appl. No. 08/619,380, filed Mar. 21, 1996, Gene H. Arts.
U.S. Appl. No. 08/621,151, filed Mar. 21, 1996, Robert B. Stoddard.
U.S. Appl. No. 08/878,694, filed Jun. 19, 1997, Lawrence K Pacer.
U.S. Appl. No. 09/270,856, filed Mar. 17, 1999, Gene H. Arts.
U.S. Appl. No. 09/504,640, filed Feb. 16, 2000, James Steven Cunningham.
U.S. Appl. No. 09/666,312, filed Sep. 21, 2000, Robert C. Platt.
U.S. Appl. No. 14/085,339, filed Nov. 20, 2013, Friedrichs et al.
U.S. Appl. No. 14/155,636, filed Jan. 15, 2014, Koo.
U.S. Appl. No. 14/157,254, filed Jan. 16, 2014, Koo.
U.S. Appl. No. 14/159,758, filed Jan. 21, 2014, Sartor.
U.S. Appl. No. 14/164,785, filed Jan. 27, 2014, Collins.
ESR14154626.7 dated Dec. 17, 2014, 9 pages.
Ward et al., "A Significant New Contribution to Radical Head and Neck Surgery"; Arch Otolaryngology, Head and Neck Surg., vol. 115 pp. 921-923 (Aug. 1989).
Lieberman et al., "Capacitive Discharges", Principles of Plasma Discharges and Materials Processing, John Wiley & Son, Inc. (2005) pp. 387-460.
Moore et al., "Confined Geometry Interactions of Downstream RF-Excited Atmospheric Plasma Wires", IEEE Transactions on Plasma Science, 0093-3813, (2008) pp. 1-2.
Walsh et al., "Contrasting Characteristics of Pulsed and Sinusoidal Cold Atmospheric Plasma Jets", Applied Physics Letters, 88, 171501 (2006) pp. 1-3.
Cho et al., "Coplanar ac Discharges Between Cylindrical Electrodes With a Nanoporous Alumina Dielectric: Modular Dielectic Barrier Plasma Devices", IEEE Transactions on Plasma Science, vol. 33, No. 2, (Apr. 2005) pp. 378-379.
Xu et al., "DBD Plasma Jet in Atmospheric Pressure Argon", IEEE Transactions on Plasma Science, vol. 36, No. 4, (Aug. 2008), pp. 1352-1353.
Alfred Grill, "Electron Cyclotron Resonance Plasmas", Cold Plasma in Materials Fabrication, IEEE Press (1994) pp. 40-43.
Brand et al., "Electrosurgical Debulking of Ovarian Cancer: A New Technique Using the Argon Beam Coagulator"; Gynecologic Oncology 39 pp. 115-118 (1990).
Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Brian Chapman, "Matching Networks", Glow Discharge Processes, John Wiley & Sons Inc., NY, (1980) pp. 153-172.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.

(56) References Cited

OTHER PUBLICATIONS

Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.

Stoffels et al., "Plasma Needle for in Vivo Medical Treatment: Recent Developments and Perspectives", Plasma Sources Science and Technology 15 (2006) pp. 169-180.

Schaper et al., "Plasma Production and Vapour Layer Production at a Pulse Power Electrode in Saline Solution:", (2008) www.escampig2008.csic.es/PosterSessions/100.

Akitsu et al., "Plasma Sterilization Using Glow Discharge at Atmospheric Pressure", Surface & Coatings Technology 193, (2005) pp. 29-34.

Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.

Brian Chapman, "Secondary Electron Emission", Glow Discharge Processes, John Wiley & Sons Inc., NY, (1980) pp. 82-138.

Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.

Lieberman et al., "Sheaths", Principles of Plasma Discharges and Materials Processing, John Wiley & Son, Inc. (2005) pp. 11-14.

Farin et al., Technology of Argon Plasma . . . Endoscopic Applications; Endoscopic Surgery and Allied Technologies, No. 1, vol. 2, pp. 71-77 (Feb. 1994).

Lieberman et al., "The Collisionless Sheath", Principles of Plasma Discharges and Materials Processing, John Wiley & Son, Inc. (2005) pp. 167-206.

Gupta et al., "The Potential of Pulsed Underwater Streamer Discharges as a Disinfection Technique", IEEE Transactions on Plasma Science, vol. 36, No. 4, (Aug. 2008) pp. 1621-1632.

Mark H. Mellow, "The Role of Endoscopic Laser Therapy in Gastrointestinal Neoplasms"; Advanced Therapeutic Endoscopy, pp. 17-21, (1990).

Silverstein et al., "Thermal Coagulation Therapy for Upper Gastrointestinal Bleeding"; Advanced Therapeutic Endoscopy, pp. 79-84, 1990.

Sobolewski, Mark A., "Current and Voltage Measurements in the Gaseous Electronics Conference RF Reference Cell". J. Res. Natl. Inst. Stand. Technol. 100, 341; Apr. 1995.

Hernandez et al., "A Controlled Study of the Argon Beam Coagultor for Partial Nephrectomy"; The Journal of Urology, vol. 143, May (1990) J. Urol. 143: pp. 1062-1065.

\* cited by examiner

SYSTEM AND METHOD FOR TREATMENT OF BIOFILMS

CROSS REFERENCE TO RELATED APPLICATION

The present application claims the benefit of and priority to U.S. Provisional Application Ser. No. 61/763,265, filed on Feb. 11, 2013, the entire contents of which are incorporated herein by reference.

BACKGROUND

1. Technical Field

The present disclosure relates to plasma devices and processes for surface processing, removal or deposition of biological or other materials. More particularly, the disclosure relates to an apparatus and method for generating and directing chemically reactive, plasma-generated species in a plasma device along with excited-state species (e.g., energetic photons) that are specific to the selected ingredients.

2. Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including vacuum ultraviolet photons that have sufficient energy to initiate photochemical and photocatalytic reaction paths in biological and other materials that are irradiated by the plasma photons.

SUMMARY

Plasmas have broad applicability to provide alternative solutions to industrial, scientific and medical needs, especially workpiece surface processing at low temperature. Plasmas may be delivered to a workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Selective plasmas may also remove a distinct upper layer of a workpiece but have little or no effect on a separate underlayer of the workpiece or it may be used to selectively remove a particular tissue type from a mixed tissue region or selectively remove tissue with minimal effect to adjacent organs of different tissue type, e.g., removal of extra cellular matrix.

One suitable application of the unique chemical species is to drive non-equilibrium or selective chemical reactions at or within the workpiece to provide for selective removal of only certain types of materials. Such selective processes are especially sought in biological tissue processing (e.g., mixed or multi-layered tissue), which allows for cutting and removal of tissue at low temperatures with differential selectivity to underlayers and adjacent tissues. This is particularly useful for removal of extra cellular matrices, biofilms, mixtures of fatty and muscle tissue, and debridement of surface layers.

Biofilms are an aggregate of microorganisms (e.g., bacteria) that may be embedded in a self-produced matrix of extracellular polymeric substances. In particular, a biofilm colony creates a polymer chain between the populations of bacteria, allowing the colony to adhere to various types of surfaces, including live tissue. Biofilm growth on living tissue is believed to present a variety of health problems, such as infections, toxic shock syndrome, crystallized kidneys and heart valve problems. Pathogenic biofilms are also commonly found on implanted medical devices, resulting in reinfection problems for artificial joints or bone and tooth implants. Biofilms are resistant to chemical bactericides since biofilms regenerate very rapidly and develop resistance to applied bactericides. In addition, biofilm colonies can alter the outer surface (e.g., polymer chains) to better protect the bacteria inside the coating, further enhancing their survival.

The plasma species are capable of modifying the chemical nature of tissue surfaces by breaking chemical bonds, substituting or replacing surface-terminating species (e.g., surface functionalization) through volatilization, gasification or dissolution of surface materials (e.g., gas and liquid base etching). With proper techniques, material choices and conditions, one can selectively remove one type of tissue entirely without affecting a nearby different type of tissue. Controlling plasma conditions and parameters (including S-parameters, V, I, $\Theta$, and the like) allows for the selection of a set of specific plasma particles, which, in turn, allows for selection of chosen chemical pathways for material removal or modification as well as selectivity of removal of desired tissue type. The present disclosure provides for a system and method for creating plasma under a broad range of conditions including tailored geometries, various plasma feedstock media, number and location of electrodes and electrical excitation parameters (e.g., voltage, current, phase, frequency, pulse condition, etc.), all of which affect selectivity of the plasma to the plasma irradiated work piece.

The supply of electrical energy that ignites and sustains the plasma discharge is delivered through substantially conductive electrodes that are icapacitively and/or inductively coupled with the ionizable media and other plasma feedstocks. The present disclosure also provides for methods and apparatus that utilize specific electrode structures that improve and enhance desirable aspects of plasma operation such as higher electron temperature, greater catalytic effect on feedstocks and higher amount of secondary emission, In particular, the present disclosure provides for porous media controlled release of chemical reactants and for holding catalytic materials.

The plasma includes electrons, radicals, metastable species and photons that drive the reaction at the workpiece, including energetic electrons delivered thereto. Controlling plasma conditions and parameters allows for selection of a set of specific particles, which, in turn, allows for selection of chemical pathways for material removal or modification as well as selectivity of removal of desired tissue type. The present disclosure also provides for a system and method for generating plasmas that operate at or near atmospheric pressure. The plasmas include electrons and photons that drive reactions at material surfaces in concert with other plasma species. Electrons and photons delivered to the material surface can initiate a variety of processes including bond scission, which enables volatilization in subsequent reactions. Tailored plasmas may enhance polymerization of monomers. The electron-driven reactions act synergistically with associated fluxes to achieve removal rates of material greater than either of the reactions acting alone.

According to one embodiment of the present disclosure, a plasma system is disclosed. The system includes a plasma device including an inner electrode and an outer electrode coaxially disposed around the inner electrode, wherein at least one of the inner electrode and the outer electrode is temperature controlled; an ionizable media source coupled to the plasma device and configured to supply ionizable media thereto; and a power source coupled to the inner and outer electrodes and configured to ignite the ionizable media at the plasma device to form a plasma effluent.

According to one aspect of the above embodiment, at least one of the inner electrode and the outer electrode is formed from a metal alloy and includes a dielectric coating covering at least a portion thereof.

According to one aspect of the above embodiment, the system further includes: a coolant assembly including: a supply source configured to store a coolant fluid; and a supply tank coupled to the supply source and configured to circulate to coolant fluid through at least one of the inner electrode and the outer electrode.

According to one aspect of the above embodiment, the coolant assembly further includes a temperature controller having a temperature sensor configured to measure temperature and a cooler, wherein the cooler is configured to maintain a predetermined temperature as a function of the measured temperature.

According to one aspect of the above embodiment, the inner electrode has a substantially cylindrical tubular structure defining a lumen therein, the lumen being in fluid communication with the coolant assembly.

According to one aspect of the above embodiment, the plasma device further includes a coolant chamber having a substantially cylindrical tubular-shaped housing having an inner lumen configured to be slidably disposed over the outer electrode and a coolant lumen configured to be coupled to the coolant assembly.

According to one aspect of the above embodiment, the cylindrical tubular-shaped housing includes an outer housing and an inner housing having a coolant lumen defined therebetween.

According to one aspect of the above embodiment, the coolant lumen has a substantially helical coil shape.

According to one embodiment of the present disclosure, a plasma device configured to receive ionizable media is disclosed. The plasma device includes: an outer electrode having a substantially cylindrical tubular shape; an inner electrode coaxially disposed within the outer electrode, the inner electrode having a substantially cylindrical tubular structure defining a lumen therein, the lumen configured to couple to a coolant assembly; and a coolant chamber having a substantially cylindrical tubular-shaped housing having an inner lumen configured to be slidably disposed over the outer electrode and a coolant lumen configured to be coupled to the coolant assembly.

According to one aspect of the above embodiment, the cylindrical tubular-shaped housing includes an outer housing and an inner housing having a coolant lumen defined therebetween.

According to one aspect of the above embodiment, the coolant lumen has a substantially helical coil shape.

According to one aspect of the above embodiment, at least one of the inner electrode and the outer electrode is formed from a metal alloy and includes a dielectric coating covering at least a portion thereof.

According to one aspect of the above embodiment, the dielectric coating is selected from the group consisting of an oxide, a nitride, a native oxide and a native nitride;

According to one aspect of the above embodiment, the metal alloy is selected from the group consisting of an aluminum alloy and a titanium alloy.

According to one embodiment of the present disclosure, a plasma system is disclosed. The system includes a plasma device including an inner electrode and an outer electrode coaxially disposed around the inner electrode, wherein at least one of the inner electrode and the outer electrode is temperature controlled; an ionizable media source coupled to the plasma device and configured to supply ionizable media thereto; a power source coupled to the inner and outer electrodes and configured to ignite the ionizable media at the plasma device to form a plasma effluent. The system also includes a coolant assembly including: a supply source configured to store a coolant fluid; and a supply tank coupled to the supply source and configured to circulate to coolant fluid through at least one of the inner electrode and the outer electrode.

According to one aspect of the above embodiment, the coolant assembly further includes a temperature controller having a temperature sensor configured to measure temperature and a cooler, wherein the cooler is configured to maintain a predetermined temperature as a function of the measured temperature.

According to one aspect of the above embodiment, the inner electrode has a substantially cylindrical tubular structure defining a lumen therein, the lumen being in fluid communication with the coolant assembly.

According to one aspect of the above embodiment, the plasma device further includes a coolant chamber having a substantially cylindrical tubular-shaped housing having an inner lumen configured to be slidably disposed over the outer electrode and a coolant lumen configured to be coupled to the coolant assembly.

According to one aspect of the above embodiment, the cylindrical tubular-shaped housing includes an outer housing and an inner housing having a coolant lumen defined therebetween.

According to one aspect of the above embodiment, the coolant lumen has a substantially helical coil shape.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Plasmas are generated using electrical energy that is delivered as either direct current (DC) electricity or alternating current (AC) electricity, in either continuous or pulsed modes, at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuit that is used to deliver electrical energy to the circuit affects many properties and requirements of the plasma. The performance of the plasma chemical generation, the gas or liquid feedstock delivery system and the design of the electrical excitation circuitry are interrelated—as the choices of operating voltage, frequency and current levels, as well as phase, effect both the electron temperature and electron density. Further, choices of electrical excitation and plasma device hardware also determine how a given plasma system responds dynamically to the introduction of new ingredients to the host plasma gas or liquid media. The corresponding dynamic adjustment of the electrical drive, such as via dynamic match networks or adjustments to voltage, current, or excitation frequency may be used to maintain controlled power transfer from the electrical circuit to the plasma.

Figure 1:
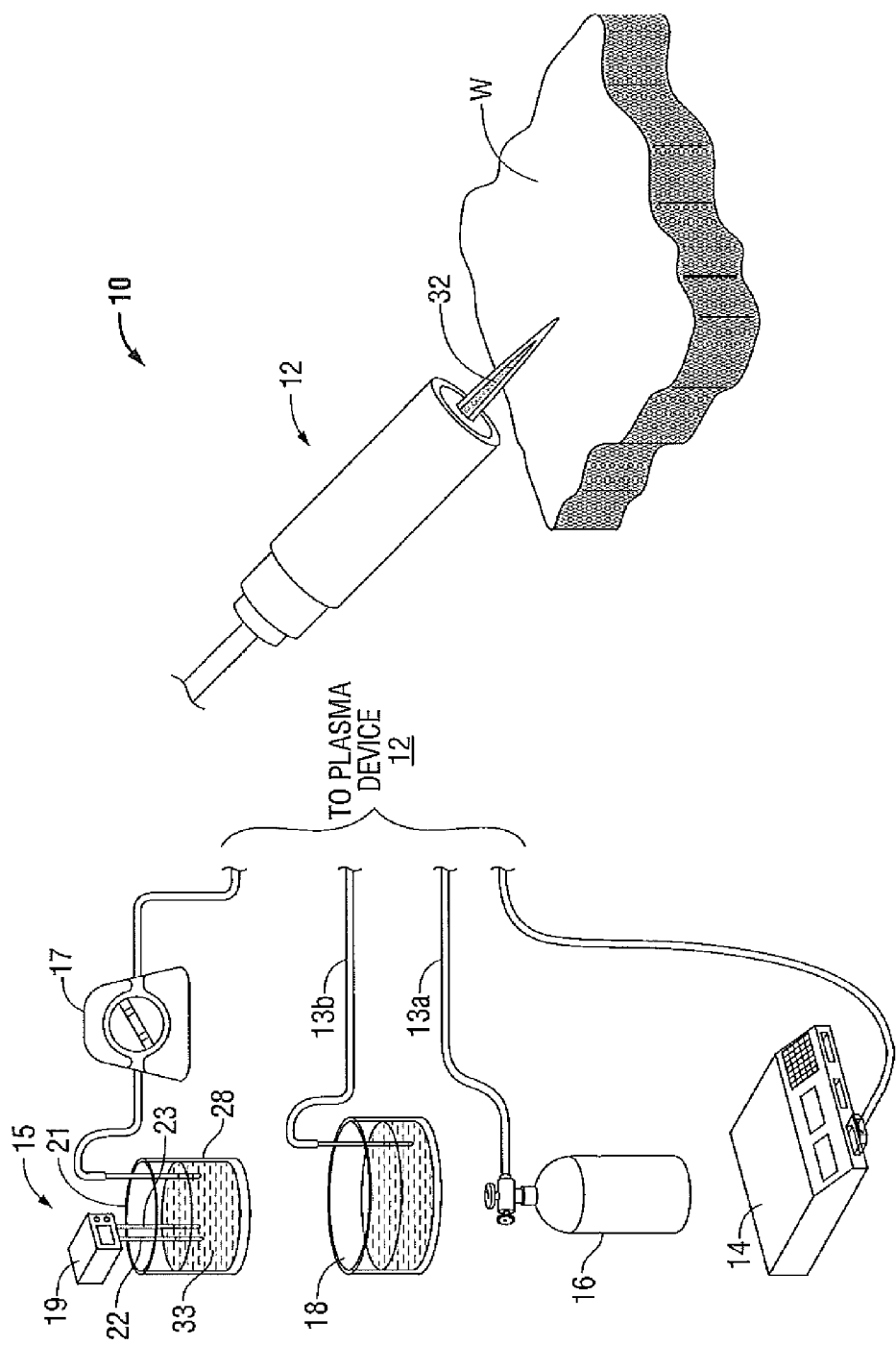
FIG. 1 is a schematic diagram of a plasma system according to the present disclosure.

Referring initially to FIG. 1, a plasma system 10 is disclosed. The system 10 includes a plasma device 12 that is coupled to a power source 14, an ionizable media source 16 and a chemical precursor or pre-ionization source 18. Power source 14 includes any suitable components for delivering power or matching impedance to plasma device 12. More particularly, the power source 14 may be any radio frequency generator or other suitable power source capable of producing electrical power to ignite and sustain the ionizable media to generate a plasma effluent 32. The plasma device 12 may be utilized as an electrosurgical pencil for application of plasma to tissue and the power source 14 may be an electrosurgical generator that is adapted to supply the device 12 with electrical power at a frequency from about 0.1 MHz to about 2,450 MHz and in another embodiment from about 1 MHz to about 160 MHz. In embodiments, electrical energy may be supplied as a mixture of two or more frequencies (e.g., 13.56 MHz & 60 MHz mixture). The plasma may also be ignited by using continuous or pulsed direct current (DC) electrical energy continuous or pulsed RF electrical energy.

The precursor source 18 may include a bubbler or a nebulizer configured to aerosolize precursor feedstocks prior to introduction thereof into the device 12. In embodiments, the precursor source 18 may also include a micro droplet or injector system capable of generating predetermined refined droplet volume of the precursor feedstock from about 1 femtoliter to about 1 milliliter in volume. The precursor source 18 may also include a microfluidic device, a piezoelectric pump, or an ultrasonic vaporizer.

The system 10 provides a flow of plasma through the device 12 to a workpiece "W" (e.g., tissue). Plasma feedstocks, which include ionizable media and precursor feedstocks, are supplied by the ionizable media source 16 and the precursor source 18, respectively, to the plasma device 12. During operation, the precursor feedstock and the ionizable media are provided to the plasma device 12 where the plasma feedstocks are ignited to form plasma effluent 32 containing ions, radicals, photons from the specific excited species and metastables that carry internal energy to drive desired chemical reactions in the workpiece "W" or at the surface thereof. The feedstocks may be mixed upstream from the ignition point or midstream thereof (e.g., at the ignition point) of the plasma effluent, as shown in FIG. 1 and described in more detail below.

The ionizable media source 16 provides ionizable feedstock to the plasma device 12. The ionizable media source 16 is coupled to the plasma device 12 and may include a storage tank and a pump (not explicitly shown). The ionizable media may be a liquid or a gas such as argon, helium, neon, krypton, xenon, radon, carbon dioxide, nitrogen, hydrogen, oxygen, etc. and their mixtures, and the like. These and other gases may be initially in a liquid form that is gasified during application.

The precursor source 18 provides precursor feedstock to the plasma device 12. The precursor feedstock may be either in solid, gaseous or liquid form and may be mixed with the ionizable media in any state, such as solid, liquid (e.g., particulates, nanoparticles or droplets), gas, and the combination thereof. The precursor source 18 may include a heater, such that if the precursor feedstock is liquid, it may be heated into gaseous state prior to mixing with the ionizable media.

In one embodiment, the precursors may be any chemical species capable of forming reactive species following plasma drive dissociation such as ions, electrons, excited-state (e.g., metastable) species, molecular fragments (e.g., radicals) and the like, when ignited by electrical energy from the power source 14 or when undergoing collisions with particles (electrons, photons, or other energy-bearing species of limited and selective chemical reactivity) formed from ionizable media 16. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the chemical precursors may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as NaOH, KOH, amines, alkyls, alkenes, and the like. Such chemical precursors may be applied in substantially pure, mixed, or soluble form.

The precursors and their functional groups as well as nanoparticles may be delivered to a surface to react with the surface species (e.g., molecules) of the workpiece "W." In other words, the functional groups may be used to modify or replace existing chemical surface terminations of the workpiece "W." The functional groups react readily with the surface species due to their high reactivity and the reactivity imparted thereto by the plasma. In addition, the functional groups are also reacted within the plasma volume prior to delivering the plasma volume to the workpiece.

Some functional groups generated in the plasma can be reacted in situ to synthesize materials that subsequently form a deposition upon the surface. This deposition may be used for stimulating healing, killing bacteria, and increasing hydrophilic or hydroscopic properties to minimize tissue sticking to the electrode or to other tissue. In addition, deposition of certain function groups may also allow for encapsulation of the surface to achieve predetermined gas/liquid diffusion, e.g., allowing gas permeation but preventing liquid exchange, to bond or stimulate bonding of surfaces, or as a physically protective layer.

The ionizable media source 16 and the precursor source 18 and may be coupled to the plasma device 12 via tubing 13a and 13b, respectively. The tubing 13a and 13b may be combined into a single tubing (e.g., via a Y coupling) to deliver a mixture of the ionizable media and the precursor feedstock to the device 12 at a proximal end thereof. This allows for the plasma feedstocks, e.g., the precursor feedstocks, nanoparticles and the ionizable gas, to be delivered to the plasma device 12 simultaneously prior to ignition of the mixture therein.

In another embodiment, the ionizable media source 16 and the precursors source 18 may be coupled to the plasma device 12 via the tubing 13a and 13b at separate connections, such that the mixing of the feedstocks occurs within the plasma device 12 upstream from the ignition point. In other words, the plasma feedstocks are mixed proximally of the ignition point, which may be any point between the respective sources 16 and 18 and the plasma device 12, prior to ignition of the plasma feedstocks to create the desired mix of the plasma effluent species flux (e.g., particles/$cm^2$sec) for each specific surface treatment on the workpiece "W."

In a further embodiment, the plasma feedstocks may be mixed midstream, e.g., at the ignition point or downstream of the plasma effluent, directly into the plasma. More specifically, the tubing 13a and 13b may be coupled to the device 12 at the ignition point, such that the precursor feedstocks and the ionizable media are ignited concurrently as they are mixed (FIG. 1). It is also envisioned that the ionizable media may be supplied to the device 12 proximally of the ignition point, while the precursor feedstocks are mixed therewith at the ignition point.

In a further illustrative embodiment, the ionizable media may be ignited in an unmixed state and the precursors may be mixed directly into the ignited plasma. Prior to mixing, the plasma feedstocks may be ignited individually. The plasma feedstock is supplied at a predetermined pressure to create a flow of the medium through the device 12, which aids in the reaction of the plasma feedstocks and produces a plasma effluent. The plasma according to the present disclosure is generated at or near atmospheric pressure under normal atmospheric conditions.

Figure 4:
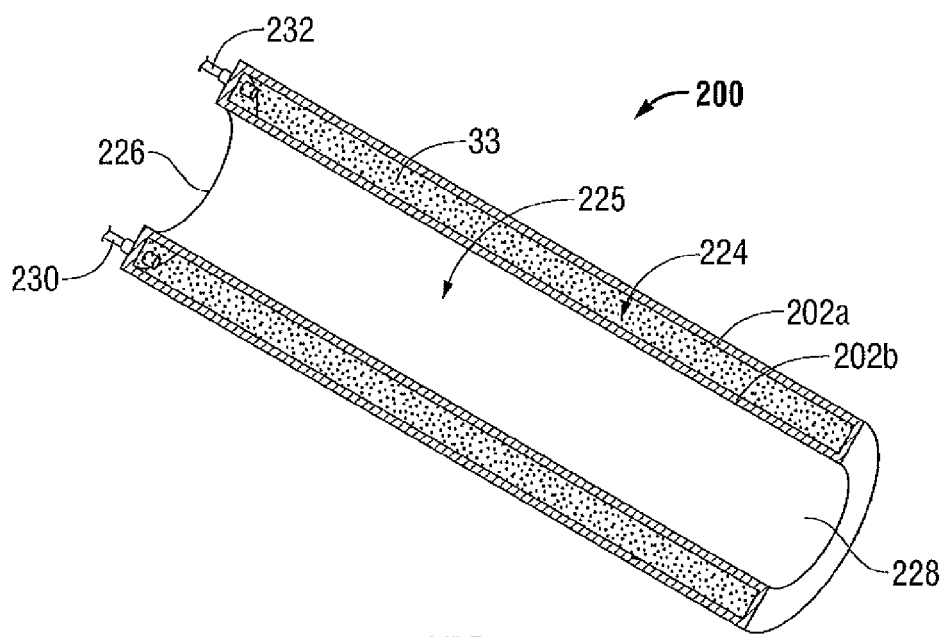
FIG. 4 is a perspective, cross-sectional view of a coolant chamber of the plasma device of FIG. 2 according to one embodiment the present disclosure.

The system 10 also includes a coolant assembly 15 for cooling the device 12 and particularly the plasma effluent 32. The coolant assembly 15 includes a supply pump 17 and a supply source (e.g., tank, bag, etc.) 21 for supplying a coolant fluid 33 to the device 12 (FIG. 4). The supply pump 17 may be of any suitable type of pump known in the art configured to circulate the coolant fluid 33 through the device 12. In embodiments, the pump 17 may generate negative pressure within the coolant fluid passages, namely, coolant lumens 124, 224, 324, inlet tubes 120, 230, 330 and outlet tubes 132, 232, 332 see FIGS. 2, 4 and 5 respectively). The negative pressure prevents the leakage of the coolant fluid 33 through any potential breaches within the coolant lumens 124, 224, 324, inlet tubes 120, 230, 330 and outlet tubes 132, 232, 332, thus minimizing the likelihood of leaks within sterile fields.

The coolant fluid may be a gas and/or a mixture of fluid and gas. The supply tank 17 stores the coolant fluid 33 and, in one embodiment, may maintain the fluid at a predetermined temperature (e.g., −10° C.). The coolant fluid 33 may be a dielectric fluid to prevent shorting of the device 12, such as deionized water, propylene glycol, ethylene glycol, combinations thereof, and the like. The coolant assembly 15 includes a temperature controller 19 (e.g., immersion circulator) having a temperature sensor 23 (e.g., temperature probe, thermistor, thermocouple) in communication with the coolant fluid 33. The temperature controller 19 also includes a cooler 22 for regulating the temperature of the coolant fluid 33 based on the temperature readings from the temperature sensor.

Figure 2:
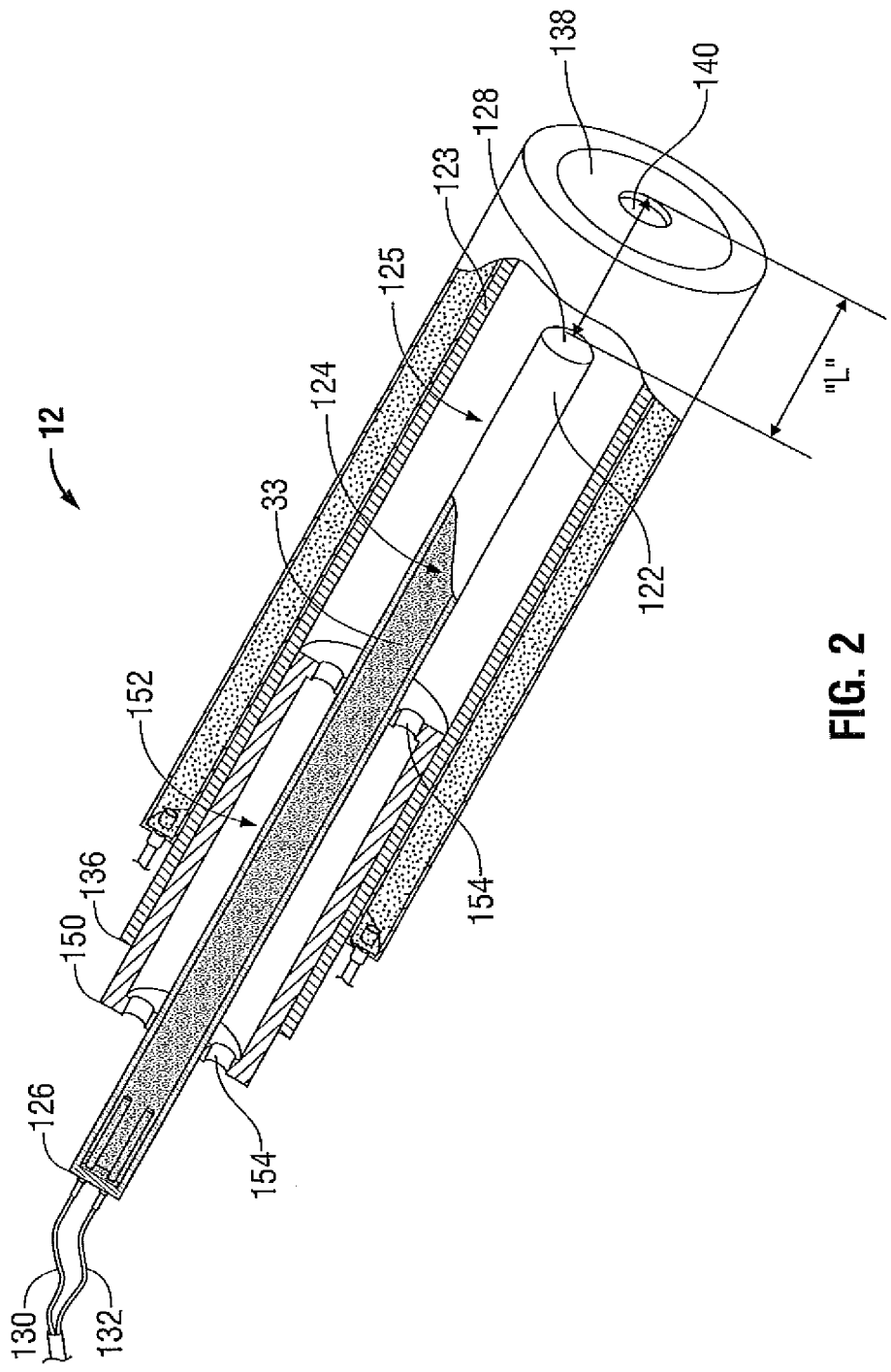
FIG. 2 is a perspective, cross-sectional view of a plasma device according to the present disclosure.
Figure 3:
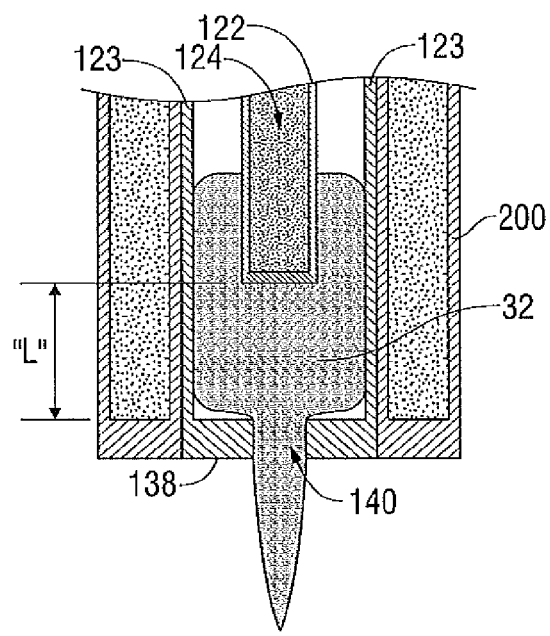
FIG. 3 is a side schematic cross-sectional view of the plasma device of FIG. 2 according to the present disclosure.

With reference to FIG. 2, the device 12 includes a temperature-controlled inner electrode 122 disposed coaxially within a temperature-controlled outer electrode 123. The inner electrode 122 has a substantially cylindrical tubular shape defining a lumen 124 therein. The inner electrode 122 includes an open proximal end 126 and a closed at a distal end 128. The inner electrode 122 is coupled to the coolant assembly 15 via one or more inlet tubes 130 and outlet tubes 132. The coolant assembly 15 circulates the coolant fluid 33 through the lumen 124, thereby cooling the inner electrode 122.

The outer electrode 123 also has a substantially cylindrical tubular shape defining a lumen 125 therein having a first diameter. The outer electrode 123 includes an open proximal end 136 and a distal end 138. The distal end 138 includes a centrally disposed opening 140 defined therein. The opening 140 has a second diameter that is smaller than the first diameter of the lumen 125, allowing for the plasma effluent 32 to flow therethrough at a faster velocity.

The electrodes 122 and 123 may be formed from a conductive material suitable for ignition of plasma such as metals and metal-ceramic composites. In one embodiment, the electrodes 122 and 123 may be formed from a conductive metal including a native oxide or nitride compound disposed thereon.

The device 12 also includes an electrode spacer 150 disposed between the inner and outer electrodes 122 and 123. The electrode spacer 150 may be disposed at any point between the inner and outer electrodes 122 and 123 to provide for a coaxial configuration between the inner and outer electrodes 122 and 123. The electrode spacer 150 includes a central opening 152 adapted for insertion of the inner electrode 122 therethrough and one or more flow openings 154 disposed radially around the central opening 152 to allow for the flow of ionizable media and precursors through the device 12. The electrode spacer 150 may be frictionally fitted to the electrodes 122 and 123 to secure the inner electrode 122 within the outer electrode 123. The electrode spacer 150 may be formed from a dielectric material, such as ceramic, to provide capacitive coupling between the inner and outer electrodes 122 and 123.

In another embodiment, the electrode spacer 150 is slidably disposed over the inner electrode 122. This configuration provides for longitudinal adjustment of the distal portion 124 of the inner electrode 122 relative to the outer electrode 123 to achieve a desired spatial relationship between the electrodes 122 and 123 (e.g., controlling the exposure of the distal portion 124 of the inner electrode 122). In particular, this allows for adjustment of a distance "L" between the distal end 128 of the inner electrode and the distal end 138 of the outer electrode 123, in particular, the opening 140. Adjustment of the distance "L" provides for control over the length of the plasma effluent 32 exiting through the opening 140. The distance "L" may be from about 200 µm to about 2000 µm, in embodiments from about 300 µm to about 1500 µm. The distance "L" that results in the longest plasma effluent 32 may be from about 800 µm to about 1200 µm, in embodiments, from about 950 µm to about 1010 µm. The shortest and longest distance "L" may result in non-optimal lengths of the plasma effluent 32. More specifically, shortening the distance "L" decreases the space within the lumen 125, thus impeding the space within the lumen 125 for the generation of the plasma effluent 32. Conversely, lengthening the distance "L" increases the space, preventing the effluent 32 from opening 140.

One of the electrodes 122 and 123 may be an active electrode and the other may be a neutral (e.g., indifferent) or return electrode to facilitate in RF energy coupling through a balanced isolation transformer (not shown) disposed within the generator 14 to provide electrical isolation with the workpiece "W." Each of the electrodes 122 and 123 is coupled to the power source 14 that drives plasma generation, such that the energy from the power source 14 may be used to ignite the plasma feedstocks flowing through the device 12. More specifically, the ionizable media and the precursors flow through the device 12 through the openings 154 and the lumen 125 (e.g., through the electrode spacer 150 and between the inner and outer electrodes 122 and 123). When the electrodes 122 and 123 are energized, the plasma feedstocks are ignited and form the plasma effluent 32 which is emitted from the distal end of the device 12 onto the workpiece "W."

In embodiments, the inner electrode 122 and outer electrode 123 may include a coating formed from an insulative or semiconductive material deposited as a film unto the inner conductor (e.g., atomic layer deposition) or as a dielectric sleeve or layer. The coating is disposed on the outer surface of the inner electrode 122 and on the inner surface of the outer electrode 123. In other words, the surfaces of the inner and outer electrodes 122 and 123 facing the lumen 125 include the coating. In one embodiment, the coating may cover the entire surface of the inner and outer electrodes 122 and 123 (e.g., outer and inner surface thereof, respectively). In another embodiment, the coating may cover only a portion of the electrodes 122 and 123.

The coating may be a nanoporous native oxide, or a native nitride of the metal from which the inner and outer electrodes are formed, or may be a deposited layer or a layer formed by ion implantation. In one illustrative embodiment, the inner and outer electrodes 122 and 123 are formed from an aluminum alloy and the coating is aluminum oxide $Al_2O_3$) or aluminum nitride (AlN). In another illustrative embodiment, the inner and outer electrodes 22 and 23 are formed from a titanium alloy and the coating is titanium oxide (TiO2) or titanium nitride (TiN). The coating may also be zinc oxide $(ZnO_2)$ and magnesium oxide (MgO). In embodiments, the coating may also be a non-native metal oxide or nitride, such as zinc oxide $(ZnO_2)$ and magnesium oxide (MgO).

The inner and outer electrodes 122 and 123 and the coating may also be configured as a heterogeneous system. The inner and outer electrodes 122 and 123 may be formed from any suitable electrode substrate material (e.g., conductive metal or a semi-conductor) and the coating may be disposed thereon by various coating processes. The coating may be formed on the inner and outer electrodes 122 and 123 by exposure to an oxidizing environment, anodization, electrochemical processing, ion implantation, or deposition (e.g., sputtering, chemical vapor deposition, atomic layer deposition, etc.).

In another embodiment the coating on electrodes 122 and 123 may be different on each electrode and may serve separate purposes. One coating (e.g., on the electrode 122) can be selected to promote increased secondary electron emission while coating on the other electrode (e.g., electrode 123) can be selected to promote specific chemical reactions (e.g., act as a catalyst).

In one illustrative embodiment, the coating provides for capacitive coupling between the inner and outer electrodes 122 and 123. The resulting capacitive circuit element structure provides for a net negative bias potential at the surface of the inner and outer electrodes 122 and 123, which attracts the ions and other species from the plasma effluent. These species then bombard the coating and release energetic electrons.

Materials having high secondary electron emission property, γ, in response to ion and/or photon bombardment are suitable for this task. Such materials include insulators and/or semiconductors. These materials have a relatively high γ, where γ represents the number of electrons emitted per incident bombardment particle. Thus, metals generally have a low γ (e.g., less than 0.1) while insulative and semiconductor materials, such as metallic oxides have a high γ, from about 1 to about 10 with some insulators exceeding a value of 20.

Thus, the coating acts as a source of secondary emitted electrons.

Secondary electron emission, γ, may be described by the formula (1):

$$\gamma = \Gamma_{secondary}/\Gamma_{ion} \quad (1)$$

In formula (1) γ is the secondary electron emission yield or coefficient, $\Gamma_{secondary}$ is the electron flux, and $\Gamma_{ion}$ is the ion flux. Secondary emission occurs due to the impacts of plasma species (ions) onto the coating when the ion impact collisions have sufficient energy to induce secondary electron emission, thus generating γ-mode discharges. Generally discharges are said to be in γ-mode when electron generation occurs preferentially at electrode surfaces (i.e., γ>1) instead of in the gas (an α-mode discharge). In other words, per each ion colliding with the coating, a predetermined number of secondary electrons are emitted. Thus, γ may also be thought of as a ratio of the $\Gamma_{secondary}$ (e.g., the electron flux) and $\Gamma_{ion}$ (e.g., the ion flux).

These ion collisions with the surface of the coating, in turn, provide sufficient energy for secondary electron emission to generate γ discharges. The ability of coating materials such as coating to generate γ discharges varies with several parameters, with the most influence due to the choice of materials having a high γ as discussed above. This property allows coatings to act as a source of secondary emitted electrons or as a catalytic material to enhance selected chemical reaction paths.

Over time the coating may thin or be removed during the plasma operation. In order to maintain the coating to continually provide a source of secondary emitted electrons, the coating may be continually replenished during the plasma operation. This may be accomplished by adding species that reformulate the native coating on the inner and outer electrodes 122 and 123. In one embodiment, the precursor source 18 may provide either oxygen or nitrogen gas to the device 12 to replenish to oxide or nitride coating.

With reference to FIGS. 2 and 4, the device 12 also includes a coolant chamber 200. The coolant chamber 200 has a substantially cylindrical tubular dual-walled structure. The coolant chamber 200 may be formed from a variety of suitable dielectric materials, such as rubber, silicone rubber, polytetrafluoroethylene, polypropylene, polyethylene, fluoroethylpropylene, and combinations thereof.

The coolant chamber 200 includes a substantially cylindrical tubular-shaped housing 202 having an outer housing 202a and an inner housing 202b. The housings 202a and 202b define a coolant lumen 224 therebetween. The inner housing 204 defines an inner lumen 225 that includes an open proximal end 226 and an open distal end 228, allowing for the chamber 200 to be slidably disposed over the outer electrode 123. In particular, the outer electrode 123 may be slid into the inner lumen 224 during certain procedures and may be removed during procedures where temperature control is not required. The coolant lumen 225 is coupled to the coolant assembly 15 via one or more inlet tubes 230 and outlet tubes 232. The coolant assembly 15 circulates the coolant fluid 33 through the lumen 225, thereby cooling the outer electrode 123. Since the lumen 225 has substantially tubular shape, allowing for the coolant fluid 33 to be in thermal contact with the entire outer surface of the outer electrode 123.

Figure 5:
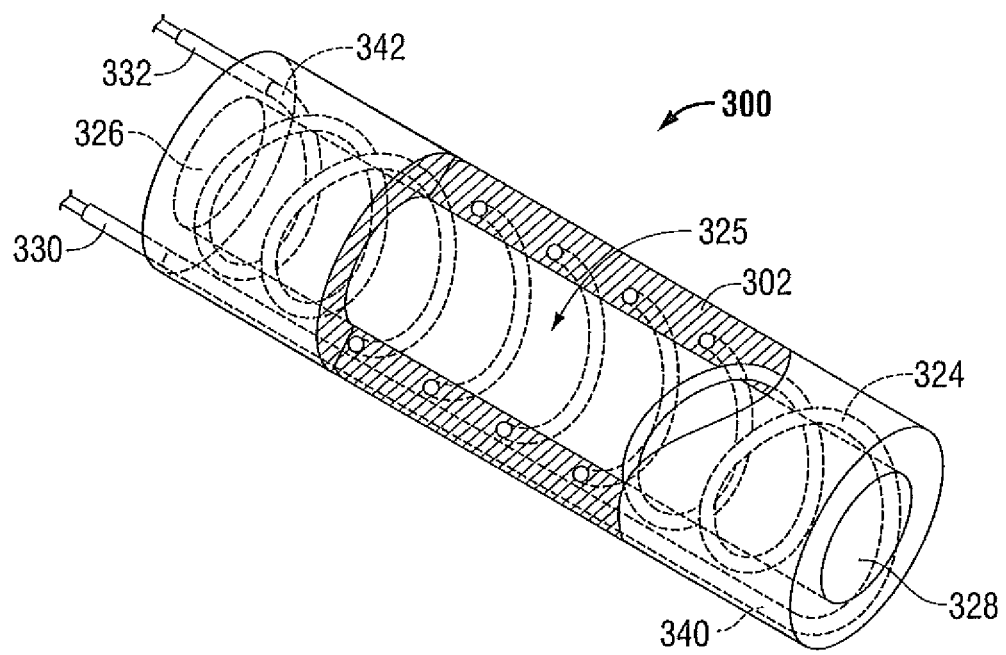
FIG. 5 is a perspective, cross-sectional view of a coolant chamber of the plasma device of FIG. 2 according to another embodiment the present disclosure.

FIG. 5 shows another embodiment of a coolant chamber 300. The coolant chamber 300 has a substantially cylindrical tubular single-walled structure. The coolant chamber 300 may be formed from a variety of suitable dielectric materials, such as rubber, silicone rubber, polytetrafluoroethylene, polypropylene, polyethylene, fluoroethylpropylene, and combinations thereof.

The coolant chamber 300 includes a substantially cylindrical tubular-shaped housing 302 defining a lumen 325. The housing 302 may be formed from a variety of suitable dielectric materials, such as rubber, silicone rubber, polytetrafluoroethylene, polypropylene, polyethylene, fluoroethylpropylene, and combinations thereof. The lumen 325 includes an open proximal end 326 and an open distal end 328, allowing for the chamber 300 to be slidably disposed over the outer electrode 123. In particular, the outer electrode 123 is slid into the lumen 325 similar to the coolant chamber 200 of FIG. 4.

The coolant chamber 300 also includes a coolant lumen 324 that is coupled to the coolant assembly 15 via one or more inlet tubes 330 and outlet tubes 332. The coolant lumen 324 may have a substantially helical coil shape having a proximal end 340 and a distal end 342. The proximal end 340 is coupled to one of the coolant tubes (e.g., inlet tube 330) and the distal end 342 is coupled to the other of the coolant tubes (e.g., outlet tube 332). This allows the coolant assembly 15 to circulate the coolant fluid 33 through the lumen 324, thereby cooling the outer electrode 123. The coolant lumen 324 may have a desired pitch (e.g., width of one complete helix turn), a larger pitch results in less turns per unit of distance, whereas a smaller pitch producers more turns. The number of turns is directly proportional to the efficiency of the heat transfer from the outer electrode 123 to the coolant fluid 33 circulating through the lumen 324.

The device 12 according to the present disclosure is suitable for biofilm removal in medical applications. The device 12 provides for low temperature and low toxicity operation. Low temperature operation is an important factor in medical applications since most biomaterials and biocompatible materials (e.g., tissue, implants) are heat-sensitive. Low toxicity operation is also an important consideration since toxicity should be minimized during any applications of plasma to live tissue to avoid any damage to healthy tissue.

The coolant fluid 33 is circulated through the inner electrode 122 as well as on the outer surface of the outer electrode 123 thereby cooling the plasma effluent 32 that is generated within the lumen 125. The temperature of the plasma effluent 32 is controlled by maintaining the temperature of the coolant fluid 33 within the supply source 21. In particular, the plasma effluent 32 and other reaction components/feedstocks are in thermal contact with the temperature-controlled electrodes 122 and 123, which cools the plasma effluent 32 prior to application thereof on the surface of the workpiece "W."

Chemical kinetics of volatilization or gasification of materials (e.g., biofilm) is directly dependent on the temperature of the media (e.g., plasma feedstocks) undergoing volatilization, namely, chemical reactions forming volatiles increase with higher temperature. Chemical reactions of the present disclosure aid in selective removal of vaporizable biofilm disposed on healthy soft or hard tissue without damaging the tissue. Therefore, a balance between low temperature operation and sufficient temperature for volatilization is also achieved by the present disclosure. Chemical kinetics are dependent on the concentration of the bioreactant (e.g., biofilm) and the concentration of the reactive radicals produced by the plasma effluent 32. Excited state radical reactions with bio-reactants are relatively fast chemical reactions that are preferred over ground-state reactions. This preference allows for reactions between excited radicals with biofilms at low temperatures. The reactions may be accomplished by locally high concentration of the excited radicals. In one illustrative embodiment, an oxygen-based plasma (e.g., oxygen gas being used as a precursor) may be used, which results in ground state atomic oxygen and oxygen metastable reacting with molecular oxygen present in the air to form ozone radicals, which is then used to gasify biofilm formations. The oxygen-based plasma also produces excited state molecular metastable singlet-delta oxygen radical, which may also be used for gasification of biofilms. The singlet-delta oxygen radicals are more safe (e.g., has a higher permissible exposure limit) than the ozone radicals without sacrificing reactivity. Therefore, the present disclosure provides for a system and method of managing the population of the oxygen-based radicals to comply with safety as well as reactivity concerns of plasma application in removing biofilm formation.

Concentrations of the singlet-delta excited oxygen radicals and the ozone radicals may be controlled by adjusting the following plasma parameters, including ionizable media flow rate, precursor gas (e.g., oxygen) flow rate, temperature of the precursor gas, excitation frequency, and loading power level. The flow rate of the oxygen gas may be from about 0.1 l/min to about 10 l/min, in embodiments from about 0.2 l/min to about 9 l/min. The temperature of the precursor gas may be from about −20° C. to about 200° C., in embodiments from about 0° C. to about 150° C. The loading power may be from about 0.01 W to about 10 KW, in embodiments from about 10 W to about 9 KW. The frequency may be from about 0.1 MHz to about 100 MHz. This allows for the oxygen radical ratios plasma effluent 32 to be adjusted to remove biofilm formations without violating safety conditions (e.g., Occupational Safety and Health Administration ("OSHA") guidelines on permissible exposure limits).

During operation, plasma feedstocks including ionizable media (e.g., argon, helium or mixtures thereof) and the precursor feedstocks (e.g., oxygen gas) are supplied to the device 12. The mixture of the plasma feedstocks is ignited and sustained by electrical energy delivered thereto through the electrodes 122 and 123. The temperature controller 19 induces a low temperature in the plasma effluent 32 and plasma feedstocks that are in contact with the cooled electrode walls. This results in cooler gas plasma feedstocks, having a temperature from about 20° C. to about 35° C., in embodiments from about 25° C. to about 30° C. as well as a cooler plasma effluent 32 that is created by a balance between cooling of the cooling system 15 and the applied electrical power that heats the plasma feedstocks. The plasma effluent 32 may be cooled to a temperature from about 10° C. to about 500° C., in embodiments, from about 25° C. to about 35° C. by varying the cooling of the temperature-controlled electrodes 122 and 123 and the plasma excitation power.

Chemical reactions induced in the plasma feedstocks include, but are not limited to disassociation (e.g., breaking up of molecular components into component parts) of plasma feedstocks and include reactive exited state radicals (e.g., singlet-delta oxygen radicals) and atom-molecule collision that form ground state reactive molecules (e.g., ozone) as well as atomic oxygen radical. The flow of the plasma feedstocks propels the resultant plasma effluent 32 having temperature-controlled plasma generated species through the opening 140 onto the biofilm.

EXAMPLE

Two stainless steel objects were used, a control object for control purposes and a test object for plasma application, were autoclaved to remove any bacterial growth. Each of the objects were placed in a mixture of about 10 ml tryptic soy broth ("TSB") and about 1 µl of biofilm-formative staphylococcus auerus ("ATCC 12600"), having a concentration of about $1.5 \times 10^4$ CFU/ml, for about 4 hours.

Approximately 1 µl of the mixture was removed to get an accurate count of the ATCC 12600 concentration. The sample was serially diluted and plated by spreading the mixture on a trypticase soy agar plate. The plate was incubated overnight (e.g., about 24 hours) and bacterial growth was then measured. The measured bacterial concentration was about $2.0 \times 10^{10}$ CFU/ml.

The objects were removed from the solution and washed with about 25 ml of phosphate-buffered saline ("PBS"). The objects were introduced into fresh TSB to reineubate the biofilm formations for about 15 hours. After the second dwell, the objects were removed and were washed again with about 25 ml of PBS to remove non-adherent bacteria from the surface. The test object was removed from the PBS using sterile forceps and placed in a sterile container for plasma application. A plasma feedstock of 1% by weight of oxygen with argon was transformed into plasma by electrical excitation at the plasma device. The plasma device was cooled by the coolant fluid at $-10°$ C. to cool the feedstock gas mixture and the resultant plasma effluent to a temperature from about 25° C. to about 35° C. The cooled plasma was used to remove biofilm from a stainless steel object. The flowing plasma-exposed area time sequence was about 0.5 cm² per minute and RF power was about 40 W at 13.56 MHz.

After treatment, the objects were tested for bacterial growth. The objects were placed in individual sterile test tubes and submerged in about 10 ml of PBS. Each object was vortexed initially for about 30 seconds within corresponding test tubes. Each object was also subjected to sonification at a frequency of about 40 kHz for about 1 minute. After sonification, each object was vortexed again for about 30 seconds within corresponding test tubes to form control and test suspensions.

An aliquot of each suspension were taken. Each of the samples was serially diluted and plated by spreading the mixture on a corresponding control and test trypticase soy agar plates. The plates were incubated overnight (e.g., about 24 hours) and bacterial growth was then measured. The measured bacterial concentration for the control object was about $1.0 \times 10^4$ CFU/ml and the test object had no detectable bacterial growth.

The test and control objects were then placed back in individual test tubes of about 10 ml TSB to assess for further growth of bacteria below the detection limit of aerobic plate counts. Test tubes were incubated overnight and checked visually for bacterial growth. The test tube containing the test object had clear TSB solution. The TSB solution of the test object was subcultured but showed no additional growth.

Figure 6:
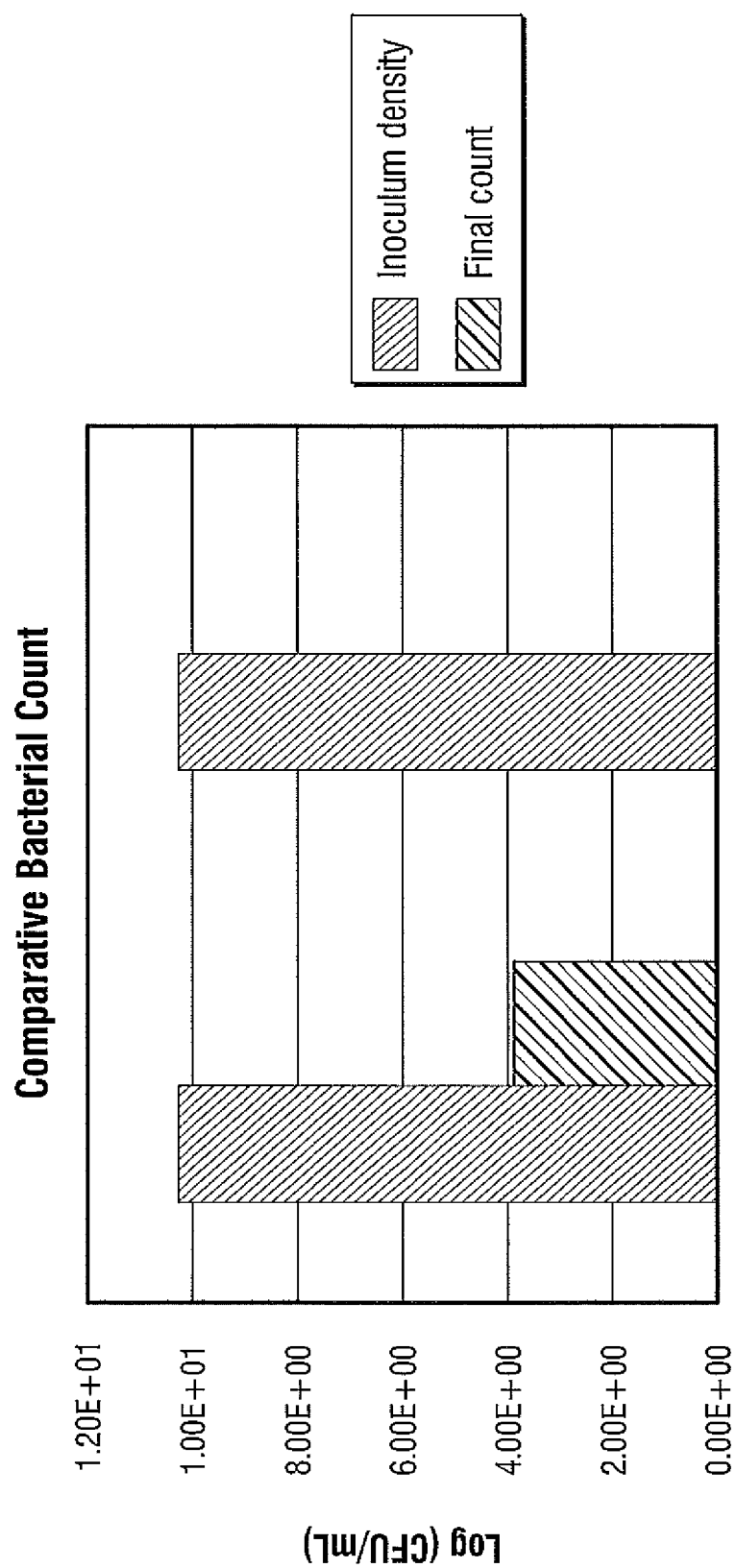
FIG. 6 is a bar graph illustrating comparative bacterial count within biofilms on treated and untreated objects.

The bacterial count of a control object (e.g., unexposed) and the treated object are shown in FIG. 6, which compares the bacterial content of the control object with that of the test object. Removal of the biofilm was complete with more than seven logs of removal with no observed regrowth after plasma exposure.

Figure 7:
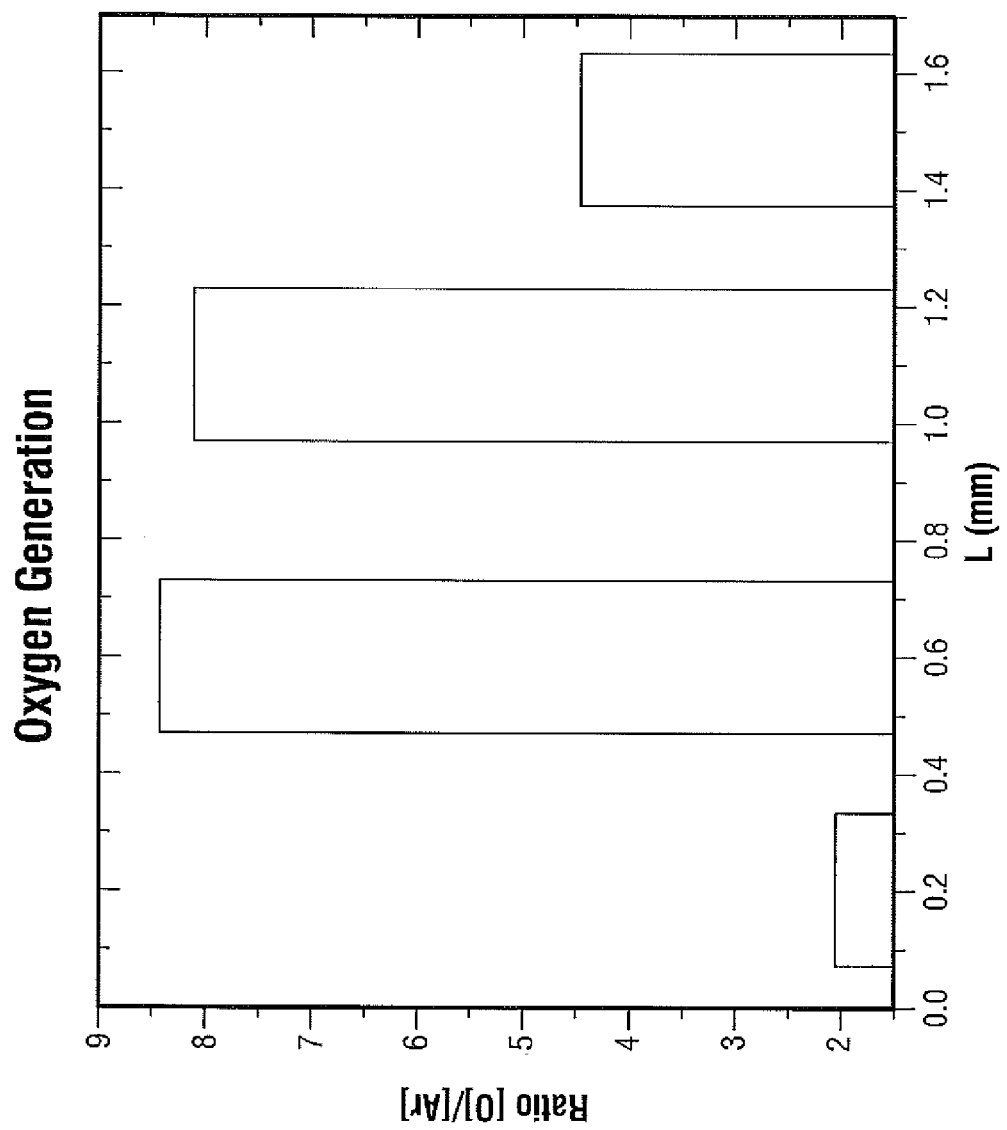
FIG. 7 is a bar graph illustrating oxygen generation based on a distance between an inner electrode and an outer electrode of the plasma device of FIG. 2 according to the present disclosure.

The distance "L" between the inner and outer electrodes was adjusted to between 200 µm and 1700 µm and oxygen radical generation was recorded as shown by the bar graphs in FIG. 7. It was demonstrated that the ratio of oxygen to argon had a peak point around the distance "L" being about 600 µm.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. In particular, as discussed above this allows the tailoring of the relative populations of reactive plasma species to meet needs for the specific process desired on the workpiece surface or in the volume of the reactive plasma.

What is claimed is:

1. A plasma system, comprising:
    a plasma device including an inner electrode and an outer electrode coaxially disposed around the inner electrode, wherein at least one of the inner electrode and the outer electrode is temperature controlled;
    an ionizable media source coupled to the plasma device and configured to supply ionizable media thereto;
    a power source coupled to the inner and outer electrodes and configured to ignite the ionizable media at the plasma device to form a plasma effluent; and
    a coolant chamber having a substantially cylindrical tubular-shaped housing having an inner lumen configured to be slidably disposed over the outer electrode and a substantially helical coil shaped coolant lumen configured to be coupled to a coolant assembly.

2. The plasma system according to claim 1, wherein at least one of the inner electrode and the outer electrode is formed from a metal alloy and includes a dielectric coating covering at least a portion thereof.

3. The plasma system according to claim 1, wherein the coolant assembly includes:
    a supply source configured to store a coolant fluid; and
    a supply tank coupled to the supply source and configured to circulate the coolant fluid through at least one of the inner electrode and the outer electrode.

4. The plasma system according to claim 3, wherein the coolant assembly further includes a temperature controller having a temperature sensor configured to measure temperature and a cooler, wherein the cooler is configured to maintain a predetermined temperature as a function of the measured temperature.

5. The plasma system according to claim 3, wherein the inner electrode has a substantially cylindrical tubular structure defining a lumen therein, the lumen being in fluid communication with the coolant assembly.

6. The plasma system according to claim 3, wherein the cylindrical tubular-shaped housing includes an outer housing and an inner housing having a coolant lumen defined therebetween.

7. A plasma device configured to receive ionizable media, comprising:
    an outer electrode having a substantially cylindrical tubular shape;
    an inner electrode coaxially disposed within the outer electrode, the inner electrode having a substantially cylindrical tubular structure defining a lumen therein, the lumen configured to couple to a coolant assembly; and
    a coolant chamber having a substantially cylindrical tubular-shaped housing having an inner lumen configured to be slidably disposed over the outer electrode and a substantially helical coil shaped coolant lumen configured to be coupled to the coolant assembly.

8. The plasma device according to claim 7, wherein the cylindrical tubular-shaped housing includes an outer housing and an inner housing having a coolant lumen defined therebetween.

9. The plasma device according to claim 7, wherein at least one of the inner electrode and the outer electrode is formed from a metal alloy and includes a dielectric coating covering at least a portion thereof.

10. The plasma system according to claim 9, wherein the dielectric coating is selected from the group consisting of an oxide, a nitride, a native oxide and a native nitride.

11. The plasma system according to claim 9, wherein the metal alloy is selected from the group consisting of an aluminum alloy and a titanium alloy.

12. A plasma system, comprising:
a plasma device including an inner electrode and an outer electrode coaxially disposed around the inner electrode, wherein at least one of the inner electrode and the outer electrode is temperature controlled;
an ionizable media source coupled to the plasma device and configured to supply ionizable media thereto;
a power source coupled to the inner and outer electrodes and configured to ignite the ionizable media at the plasma device to form a plasma effluent;
a coolant assembly including:
a supply source configured to store a coolant fluid; and
a supply tank coupled to the supply source and configured to circulate to coolant fluid through at least one of the inner electrode and the outer electrode; and
a coolant chamber having a substantially cylindrical tubular-shaped housing having an inner lumen configured to be slidably disposed over the outer electrode and a substantially helical coil shaped coolant lumen configured to be coupled to the coolant assembly.

13. The plasma system according to claim 12, wherein the coolant assembly further includes a temperature controller having a temperature sensor configured to measure temperature and a cooler, wherein the cooler is configured to maintain a predetermined temperature as a function of the measured temperature.

14. The plasma system according to claim 12, wherein the inner electrode has a substantially cylindrical tubular structure defining a lumen therein, the lumen being in fluid communication with the coolant assembly.

15. The plasma system according to claim 12, Wherein the cylindrical tubular-shaped housing includes an outer housing and an inner housing having a coolant lumen defined therebetween.

* * * * *